US012654033B2

(12) United States Patent
Yang et al.

(10) Patent No.: US 12,654,033 B2
(45) Date of Patent: Jun. 16, 2026

(54) MAGNETIC RESONANCE-GUIDED CHARGED PARTICLE BEAM RADIOTHERAPY SYSTEM

(71) Applicant: Xiangya Hospital Central South University, Changsha (CN)

(72) Inventors: Xiaoyu Yang, Changsha (CN); Hui Zhang, Changsha (CN); Zhen Yang, Changsha (CN); YIng Cao, Changsha (CN)

(73) Assignee: Xiangya Hospital Central South University, Changsha (CN)

( * ) Notice: Subject to any disclaimer, the term of this patent is extended or adjusted under 35 U.S.C. 154(b) by 131 days.

(21) Appl. No.: 18/742,751

(22) Filed: Jun. 13, 2024

(65) Prior Publication Data

US 2025/0229106 A1 Jul. 17, 2025

Related U.S. Application Data

(63) Continuation of application No. PCT/CN2024/071715, filed on Jan. 11, 2024.

(30) Foreign Application Priority Data

Jan. 11, 2024 (CN) .......................... 202410039974.4

(51) Int. Cl.
*A61N 5/10* (2006.01)
*A61B 5/055* (2006.01)
(Continued)

(52) U.S. Cl.
CPC ............ *A61N 5/1067* (2013.01); *A61B 5/055* (2013.01); *A61N 5/1049* (2013.01);
(Continued)

(58) Field of Classification Search
CPC .......... A61N 5/1067; A61N 2005/1055; A61N 2005/1087; A61N 2005/1089; A61B 5/055; G01R 33/3875; G01R 33/421
See application file for complete search history.

(56) References Cited

U.S. PATENT DOCUMENTS 8,331,531 B2 * 12/2012 Fahrig ................ G01R 33/4808
378/65
2009/0234219 A1 * 9/2009 Kruip ................... G01R 33/381
324/318
(Continued)

*Primary Examiner* — Colin T. Sakamoto
(74) *Attorney, Agent, or Firm* — JEEN IP LAW, LLC

(57) ABSTRACT

The present disclosure provides a magnetic resonance (MR)-guided charged particle beam radiotherapy device, and an electromagnetic (EM) steering parameter commissioning method aiming at target spots. The device of the present disclosure includes: a charged particle beam EM steering device, a charged particle beam sequentially passing through a multi-stage EM steering coil set to generate a parallel charged particle beam in the same direction as a main magnetic field of MR, and an MR imaging device, including an upper and a lower group of main magnetic field coils. According to the present disclosure, the charged particle beams parallel to the main magnetic field of MR and aiming at preset targets spots can be generated, which greatly reduces the effect of the Lorentz force on the charged particle beams and enhance their dosimetric advantages, thereby improving dose delivery accuracy of the charged particle beams to target spots under MR guidance.

19 Claims, 5 Drawing Sheets

(51) Int. Cl.
  *G01R 33/3875*  (2006.01)
  *G01R 33/421*  (2006.01)
(52) U.S. Cl.
  CPC ....... *G01R 33/3875* (2013.01); *G01R 33/421*
    (2013.01); *A61N 2005/1055* (2013.01); *A61N*
      *2005/1087* (2013.01); *A61N 2005/1089*
               (2013.01)

(56)       References Cited

U.S. PATENT DOCUMENTS

| | | | | |
|---|---|---|---|---|
| 2010/0013418 A1* | 1/2010 | Kruip | ..................... | A61B 5/055 |
| | | | | 250/492.3 |
| 2010/0239066 A1* | 9/2010 | Fahrig | ............... | G01R 33/4808 |
| | | | | 324/309 |
| 2011/0012593 A1* | 1/2011 | Shvartsman | ....... | G01R 33/4808 |
| | | | | 324/307 |
| 2013/0261430 A1* | 10/2013 | Uhlemann | .......... | A61N 5/1077 |
| | | | | 378/65 |
| 2016/0213951 A1* | 7/2016 | Uhlemann | ........... | A61N 5/1067 |
| 2016/0263404 A1* | 9/2016 | Mougenot | .......... | G01R 33/4814 |
| 2017/0080253 A1* | 3/2017 | Clayton | .............. | A61N 5/1067 |
| 2017/0120075 A1* | 5/2017 | Overweg | ............ | A61N 5/1081 |
| 2018/0098713 A1* | 4/2018 | Forton | .................... | A61B 5/055 |
| 2019/0027339 A1* | 1/2019 | Kamiguchi | .......... | A61N 5/1048 |
| 2019/0168028 A1* | 6/2019 | Dempsey | ............. | A61N 5/1077 |
| 2021/0154495 A1* | 5/2021 | Fujii | .................... | A61N 5/1039 |
| 2021/0393983 A1* | 12/2021 | Ni | ......................... | A61N 5/1049 |
| 2022/0280811 A1* | 9/2022 | Yamaguchi | .......... | A61N 5/1048 |

\* cited by examiner

1

MAGNETIC RESONANCE-GUIDED CHARGED PARTICLE BEAM RADIOTHERAPY SYSTEM

CROSS-REFERENCE TO RELATED APPLICATIONS

This application is a continuation of PCT/CN2024/071715, filed Jan. 11, 2024 and claims priority of Chinese Patent Application No. 202410039974.4, filed on Jan. 11, 2024, the entire contents of which are incorporated herein by reference.

TECHNICAL FIELD

The present disclosure relates to the technical field of radiotherapy devices, and in particular to a magnetic resonance (MR)-guided charged particle beam radiotherapy system, including an MR-guided parallel charged particle beam radiotherapy device and an electromagnetic (EM) steering parameter commissioning method aiming at target spot coordinates.

BACKGROUND

Cancer is the leading cause of death in humans, and about half or more of patients with cancer require radiation therapy (radiotherapy). Compared with conventional cone-beam computed tomography (CT)-guided radiotherapy, MR-guided radiotherapy has no imaging radiation dose and is able to perform MR imaging before or during patient treatment, which improves the ability to discriminate soft tissues such as tumors, provides higher treatment precision, improves the treatment efficiency of patients, and has important clinical significance.

Currently, all clinically used MR-guided radiotherapy technologies are photon radiotherapy, such as MRIdian from ViewRay of America and Unity from Elekta of Sweden. Compared with photon radiotherapy, charged particle radiotherapy has specific advantages, such as insensitivity to tissue inhomogeneity and steeper longitudinal dose fall-off of a beam, but there is no MR-guided charged particle radiotherapy equipment in clinical currently. A charged particle beam transported in a main magnetic field of MR is affected by the Lorentz force, and the beam deviates from the original direction, causing the beam to accurately locate a tumor target spot with much difficulty, resulting in missing irradiation of a tumor or false irradiation of normal tissues, and ultimately affecting the curative efficacy.

An MR-guided radiotherapy system with a main magnetic field of MR perpendicular to a direction of incident particles is disclosed in the inventive patent with the publication number of CN111580030A. In this patent, although a niobium-titanium alloy for shielding a magnetic field is arranged in a linear accelerator area, which can reduce the beam deflection of a particle beam outside patient's body, it is not able to solve the problem of an incident particle beam deflecting inside the patient's body. United Imaging of China and University of Wollongong of Australia all have designed radiotherapy systems with a main magnetic field of MR parallel to a central axis of a beam for MR-guided photon radiotherapy, but this solution is not suitable for a charged particle radiotherapy system. In this solution, only a beam on the central axis is parallel to the main magnetic field of MR, while beams deviating from the central axis diverge conically. For charged particle, the beam deviating from the central axis is still affected by Lorentz force, leading to a spiral motion path of the beam, which is not conducive to the precise localization by the beam. To solve this issue, the Center for Medical Radiation Physics at the University of Wollongong has proposed a complex two-step correction method for beam parameters, firstly, simulation and tabulation are performed on the basis of a homogeneous water phantom to obtain a first approximation of each target spot for each beam energy, and then Monte Carlo simulation is performed on a specific patient to obtain a large amount of parameters of a beam and position data of a corresponding target spot, according to which, a neural network model is trained to refine the results of the first approximation. The method is too complex and cumbersome for clinical translation, because tabulation and neural network training is required for each beam energy and specific patient.

SUMMARY

In view of the above, in order to solve the technical problems existing in the prior art, in which, a deflected trajectory of a charged particle beam leads to difficulty in accurately locating a tumor target area by the beam, resulting in missing or false irradiation, and the large scattering of the charged particle beam during transport results in an increased lateral penumbra and detrimental to the protection of normal tissues, in one aspect, the present disclosure provides an MR-guided charged particle beam radiotherapy device, which can generate charged particle beams parallel to a main magnetic field of MR, greatly reducing the effect of a Lorentz force on the charged particle beams, reducing the difficulty of locating a tumor target spot by an MR-guided charged particle beam, and improving the treatment precision; in another aspect, by means of a main magnetic field of MR imaging, the lateral confinement to the charged particle beams is realized to improve their lateral dose fall-off gradient, better protecting normal tissues around a tumor and reducing the probability of complications caused by radiotherapy.

To realize the above objective, the present disclosure provides the following technical solutions.

An MR-guided charged particle beam radiotherapy device is capable of generating charged particle beams parallel to a main magnetic field of MR and includes:

a charged particle beam generating device, i.e. a charged particle beam accelerator, which includes a linear accelerator, a cyclotron, or a synchrotron, and is configured for generating and accelerating a charged particle beam, allowing energy of the charged particle beam to reach an energy interval required for radiotherapy;

a charged particle beam EM steering device, including a multi-stage EM steering coil set, the charged particle beam sequentially passing through the multi-stage EM steering coil set to generate a parallel charged particle beam in the same direction as the main magnetic field of MR; and an MR imaging device, including:

main magnetic field coils of MR with central axes coinciding with that of the parallel charged particle beam, including an upper group of main magnetic field coils of MR and a lower group of main magnetic field coils of MR, an imaging and treatment area being formed therebetween, both the upper group of main magnetic field coils of MR and the lower group of main magnetic field coils of MR including imaging coils and shielding coils, the imaging coils being close to the imaging and treatment area, the shielding coils being away from the imaging and treatment area, and the imaging coil having a current opposite to that of the shielding coil in direction;

a gradient magnetic field coil, for generating spatial magnetic field gradient changes to facilitate layer selection and localization of imaging; and a body coil, for generating a radio-frequency field to excite proton resonance in the tissue and receive magnetic resonance relaxation signals to complete a reconstruction.

Preferably, the multi-stage EM steering coil set is a triple-stage EM steering coil set arranged sequentially from top to bottom, with each stage containing two pairs of coils that can generate orthogonal steering magnetic fields, a first-stage EM steering coil set deflecting the charged particle beam in a direction of a target spot, a second-stage EM steering coil set having a current opposite to that of the first-stage EM steering coil set in direction to correct a deflection angle of the charged particle beam, and a third-stage EM steering coil set further adjusting an incidence direction of the charged particle beam to compensate for the effect of a fringe magnetic field of MR on the incident charged particle beam, allowing the incidence direction of the charged particle beam to be consistent with the direction of the main magnetic field of the MR imaging and area.

Preferably, an interval between the upper group of main magnetic field coils of MR and the lower group of main magnetic field coils of MR is greater than 60 cm.

Preferably, charged particles in the charged particle beam are electrons, protons, carbon ions or helium ions.

In another aspect, the present disclosure provides an EM steering parameter commissioning method aiming at target spot coordinates by an MR-guided charged particle beam radiotherapy device, including the following steps:

construction of a cost function simulating, on the basis of a particle transport algorithm, a phase space of a particle beam corresponding to EM steering parameters, and constructing a cost function $\mathcal{L}_{tot}$ by means of a difference between a phase space of an ideal particle beam bombarding a target spot and the phase space of the simulated particle beam based on EM steering parameters of a current iteration, the cost function including a position cost function $\mathcal{L}_{pos}$ and a direction cost function $\mathcal{L}_{dir}$:

$$\mathcal{L}_{tot} = \mathcal{L}_{pos} + \lambda \cdot \mathcal{L}_{dir} \tag{1}$$

$$\mathcal{L}_{pos} = |x_0 - \bar{x}| + |y_0 - \bar{y}| \tag{2}$$

$$\mathcal{L}_{dir} = 1 - \cos \bar{\gamma} \tag{3}$$

where $\lambda$ is a weight coefficient of the direction cost function $\mathcal{L}_{dir}$, $x_0$ and $y_0$ are transverse coordinate positions of a target spot, $\bar{x}$ and $\bar{y}$ are average transverse coordinates of all particles of a particle beam simulated on the basis of EM steering parameters of a current iteration, and $\bar{\gamma}$ is a mean value of angles between incidence directions of all the particles of the particle beam simulated on the basis of the EM steering parameters of the current iteration and the direction of an MR main magnetic field, $\bar{x}$, $\bar{y}$ and $\bar{\gamma}$ being all determined by an EM steering parameter set $\mathcal{J}$, the parameter set $\mathcal{J}$ and the cost function $\mathcal{L}_{tot}$ having a functional relationship of $$\mathcal{L}_{tot}[\mathcal{J}; \lambda](\mathbb{R}^{2 \times N}_{(-1.0,+1.0)} \to \mathbb{R}),$$

and an EM steering parameter commissioning task being expressed as Formula (4):

$$\underset{\mathcal{J} \in \mathbb{R}^{2 \times N}_{(-1.0,+1.0)}}{\text{minimize}} \quad \mathcal{L}_{tot}[\mathcal{J}; \lambda] \tag{4}$$

where $\mathcal{J}$ is an EM steering parameter set, and N is the number of stages of the EM steering coil set;

optimization of the EM steering parameters on the basis of an optimization algorithm without gradient information randomly correcting $\mathcal{J}$ according to historical optimization results rather than using gradient information of the cost function $\mathcal{L}_{tot}[\mathcal{J}; \lambda]$ with respect to the EM steering parameter set $\mathcal{J}$ during optimization, calculating a corresponding $\mathcal{L}_{tot}[\mathcal{J}; \lambda]$, and searching for or exploring an optimization space of $\mathcal{J}$; and determination and output of an optimal steering parameter set taking an EM steering parameter set $\mathcal{J}$ with a smallest value of $\mathcal{L}_{tot}[\mathcal{J}; \lambda]$ as an optimal after the preset number of iterations is reached, and outputting an optimal EM steering parameter set of the target spot.

Preferably, the EM steering parameter set $\mathcal{J}$ includes current directions and intensities of the multi-stage EM steering coil set; and the EM steering parameter set $\mathcal{J}$ is subjected to vectorically encoded, $$\mathcal{J} = \{i_x^1, i_y^1, i_x^2, i_y^2, i_x^3, i_y^3, ...\}, \text{ where } i_x^1 \text{ and } i_y^1$$

are normalized currents of two pairs of orthogonal magnetic field coils in the first-stage EM steering coil set, the normalized currents being obtained using certain preset values, such as corresponding maximum load currents, with values ranging from −1.0 to +1.0, and positive and negative signs indicating current directions, and $$i_x^2 \text{ and } i_y^2, \text{ and } i_x^3 \text{ and } i_y^3$$

represent normalized currents in the second-stage EM steering coil and set and in the third-stage EM steering coil set, respectively.

Preferably, $\lambda$ ranges from 5.0 to 15.0.

Preferably, the optimization algorithm without gradient information is a Bayesian black-box optimization algorithm or a metaheuristic algorithm.

Preferably, the preset number of iterations is 300 or more.

Compared with the prior art, the present disclosure has the following beneficial effects.

The MR-guided charged particle beam radiotherapy device provided by the present disclosure can generate the charged particle beams parallel to the main magnetic field of MR, greatly reducing the effect of the Lorentz force on the charged particle beams, reducing the difficulty of locating the tumor target spots by the MR-guided charged particle beams, and improving the treatment precision; and by means of the main magnetic field of MR imaging, the lateral confinement to the charged particle beams is realized to improve their lateral dose fall-off gradient, better protecting the normal tissues around the tumor and reducing the probability of complications caused by radiotherapy.

BRIEF DESCRIPTION OF THE DRAWINGS

FIG. 3(*b*) shows a one-dimensional magnetic field distribution of a central axis in an imaging and treatment area;

FIG. 3(*c*) shows a two-dimensional magnetic field distribution of XZ sections of the first and second-stage steering coil set (with only a pair of steering coils in an X-direction energized);

FIG. 3(*d*) shows a one-dimensional magnetic field distribution of central axes of the first and second-stage steering coil set (with only a pair of steering coils in the X-direction energized);

FIG. 3(*e*) shows a two-dimensional magnetic field distribution of an XZ section of a third-stage steering coil set (with only a pair of steering coils in an X-direction energized); and FIG. 3(*f*) shows a one-dimensional magnetic field distribution of a central axis of the third-stage steering coil set (with only a pair of steering coils in the X-direction energized).

Figure 1:
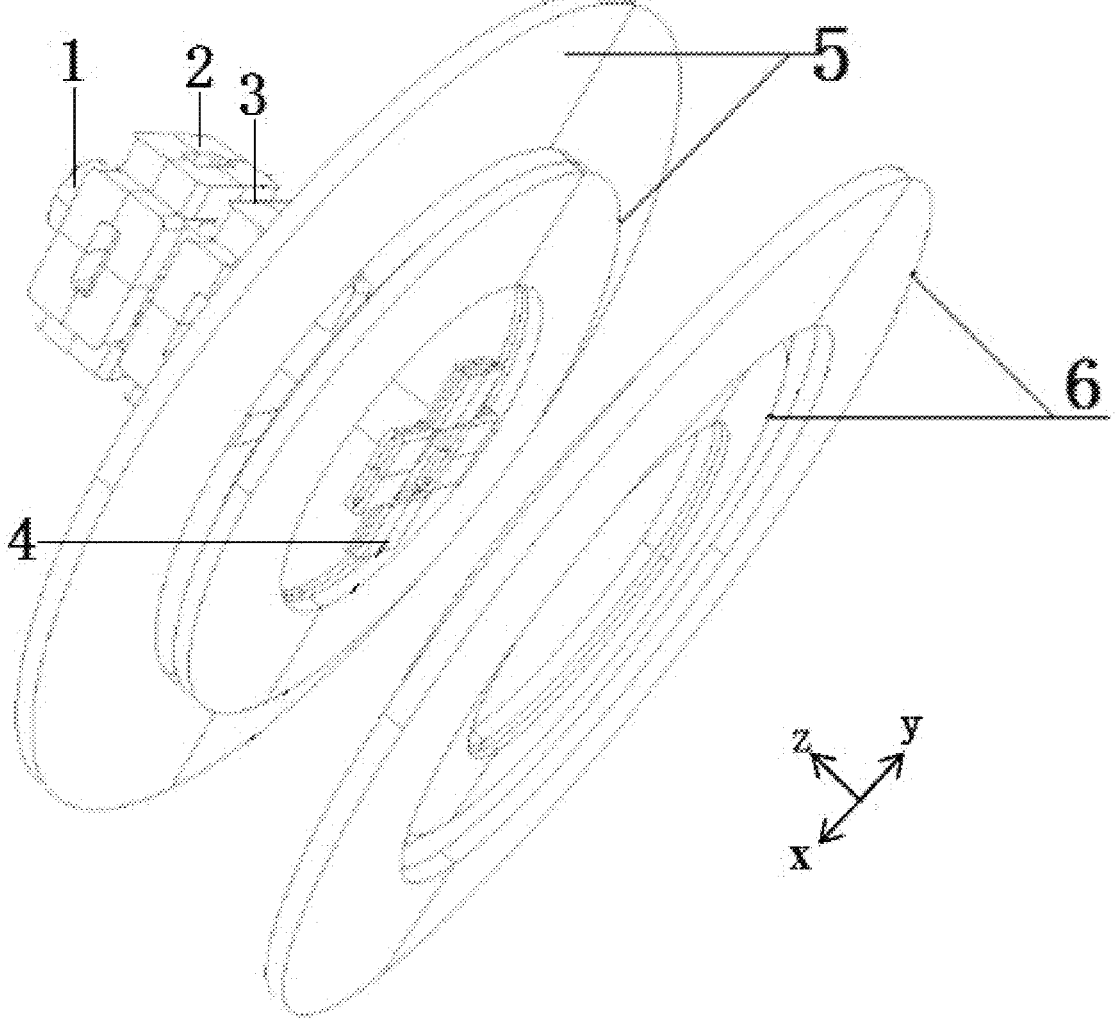
FIG. 1 is a perspective view of an MR-guided charged particle beam radiotherapy device according to the present disclosure.

Reference numerals and denotations thereof: 1—vacuum tube, 2—first-stage EM steering coil set, 3—second-stage EM steering coil set, 4—third-stage EM steering coil set, 5—upper group of main magnetic field coils of MR, and 6—lower group of main magnetic field coils of MR.

DETAILED DESCRIPTION

Technical solutions in the examples of the present disclosure will be clearly and completely described below by reference to the accompanying drawings in the examples of the present disclosure. Obviously, the examples described are only some rather than all examples of the present disclosure. On the basis of the examples of the present disclosure, all other examples obtained by those ordinary skilled in the art without creative efforts fall within the scope of protection of the present disclosure.

In the description of the present disclosure, it is to be noted that, the orientation or state relations indicated by the terms "up", "down", "inner", "outer", "top/bottom end", etc., are based on those shown in the accompanying drawings and merely for the ease of describing the present disclosure and simplifying the description, rather than indicating or implying that a device or element referred to must be in a specific orientation or constructed and operated in a specific orientation, and therefore cannot be interpreted as limiting the present disclosure. In addition, the terms "first" and "second" are only used to describe the objective, not to be understood as indicating or implying relative importance.

In the description of the present disclosure, it is to be noted that unless otherwise clearly specified and limited, the terms "mounted", "arranged", "sleeved", and "connected" are to be understood in a broad sense. For example, the "connected" can be fixedly connected, detachably connected, integrally connected, mechanically connected, electrically connected, directly connected, indirectly connected through an intermediate medium, or connected between two components. For those of ordinary skill in the art, the specific meanings of the above terms in the present disclosure can be understood according to specific circumstances.

The existing MR-guided radiotherapy technologies have the following problems.

(1) Charged particles are greatly affected by a main magnetic field and a fringe magnetic field of MR, and a trajectory of a beam is deflected or twisted, which makes it difficult for the beam to accurately locate a tumor target area, resulting in missing or false irradiation.

(2) Compared with photons, the charged particles are more likely to scatter laterally with air or human tissues, especially for lighter charged particles, such as electrons, which will scatter a lot during transport, resulting in an increased lateral penumbra, and it is not conducive to the protection of normal tissues.

The present disclosure provides an MR-guided charged particle beam radiotherapy device, which is capable of generating charged particle beams parallel to a main magnetic field of MR and includes:

a charged particle beam generating device, i.e. a particle beam accelerator, which includes a linear accelerator, a cyclotron, or a synchrotron, and is configured for generating and accelerating a charged particle beam, allowing energy of the charged particle beam to reach an energy interval required for radiotherapy;

a charged particle beam EM steering device, including a multi-stage EM steering coil set, the charged particle beam sequentially passing through the multi-stage EM steering coil set to generate a parallel charged particle beam in the same direction as the main magnetic field of MR, and unlike the off-center divergent transport of charged particle beams used in conventional radiotherapy, the parallel charged particle beam, whether its beam is on an isocenter axis or off-center axis, the direction of the beam always coinciding with that of the main magnetic field of the MR; and an MR imaging device, including:

main magnetic field coils of MR with central axes coinciding with that of the parallel charged particle beams, including an upper group of main magnetic field coils of MR and a lower group of main magnetic field coils of MR, an imaging and treatment area being formed therebetween, both the upper group of main magnetic field coils of MR and the lower group of main magnetic field coils of MR including imaging coils and shielding coils, the imaging coils being close to the imaging and treatment area, the shielding coils being away from the imaging and treatment area, and the imaging coil having a current opposite to that of the shielding coil in direction;

a gradient magnetic field coil, for generating spatial magnetic field gradient changes to facilitate layer selection and localization of imaging; and a body coil, for generating a radio-frequency field to excite protons resonance in the tissue and receive magnetic resonance relaxation signals to complete a reconstruction.

Figure 2:
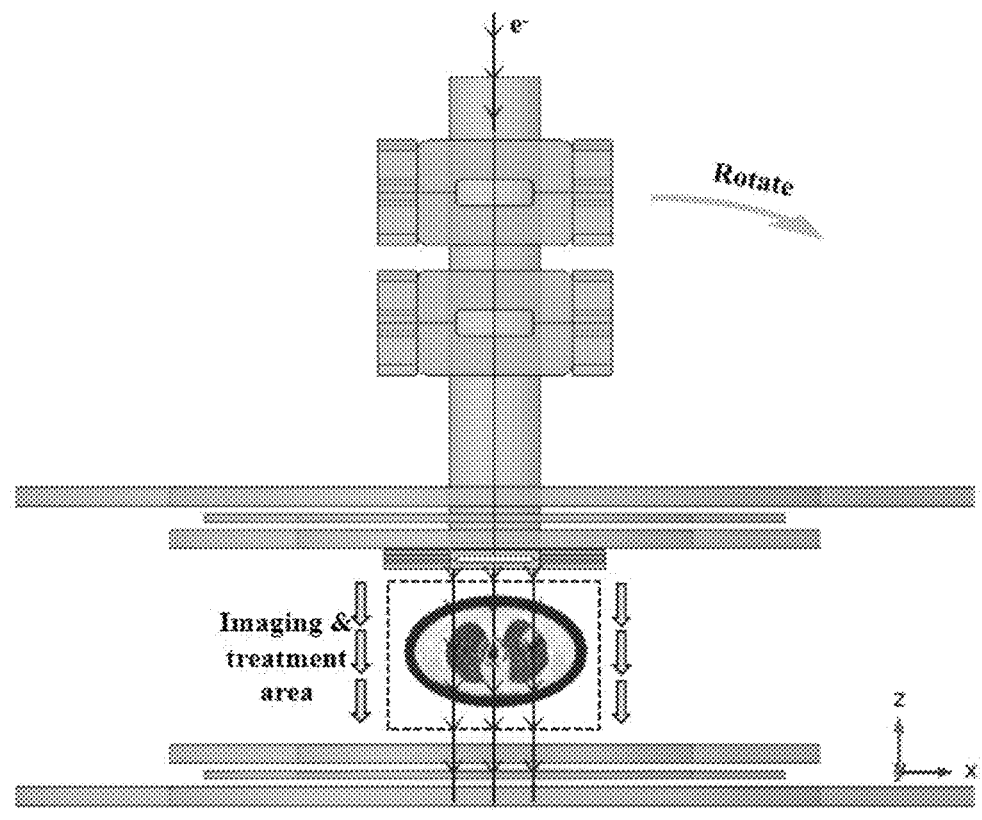
FIG. 2 is a front view of the MR-guided charged particle beam radiotherapy device according to the present disclosure.

The details are shown in FIGS. 1-2. The present disclosure exemplarily provides an MR-guided charged particle beam radiotherapy device, with a multi-stage EM steering coil set illustrated in triple stages, including:

a vacuum tube 1, a first-stage EM steering coil set 2, a second-stage EM steering coil set 3, and a third-stage EM steering coil set 4 being sequentially sleeved outside the vacuum tube 1 from top to bottom;

an upper group of main magnetic field coils of MR 5, the third-stage EM steering coil set 4, and a lower group of main magnetic field coils of MR 6, arranged sequentially from top to bottom (the third-stage EM steering coil set 4 is immediately below the upper group of main magnetic field coils of MR 5 because the third-stage EM steering coil set 4 needs to correct the effect of a fringe magnetic field generated by the upper group of main magnetic field coils of MR 5 on a beam), and an imaging and treatment area being formed between the upper group of main magnetic field coils of MR 5 and the lower group of main magnetic field coils of MR 6; and a charged particle beam generating device, i.e. a particle beam accelerator (not shown in the figure), which includes a linear accelerator, a cyclotron, or a synchrotron, and is_capable of generating a charged particle beam, the charged particle beam after being accelerated by an accelerating device and delivered along the vacuum tube 1 to the imaging and treatment area.

The device can greatly reduce the deflection or distortion of an incident trajectory of the charged particle beam caused by the main magnetic field and fringe magnetic field of MR, and at the same time, confine the lateral scattering of the charged particle beam and reduce a lateral penumbra, realizing the precise localization by an MR-guided charged particle beam, and improving the radiotherapy precision.

In the present disclosure, the multi-stage EM steering coil set is a triple-stage EM steering coil set arranged sequentially from top to bottom with each stage containing two pairs of coils that can generate orthogonal steering magnetic fields.

A first-stage EM steering coil set 2 deflects the charged particle beam in a direction of a target spot. A second-stage EM steering coil set $\mathcal{J}$ has a current opposite to that of the first-stage EM steering coil set 2 to correct a deflection angle of the charged particle beam. A third-stage EM steering coil set 4 further adjusts an incidence direction of the charged particle beam to compensate for the effect of a fringe magnetic field of MR on an incident charged particle beam, allowing the incidence direction of the charged particle beam to be consistent with the direction of the main magnetic field of the MR imaging area.

In the present disclosure, an interval between the upper group of main magnetic field coils of MR 5 and the lower group of main magnetic field coils of MR 6 is greater than 60 cm.

In the present disclosure, charged particles in the charged particle beam are electrons, protons, carbon ions or helium ions.

In another aspect, the present disclosure provides an EM steering parameter commissioning method aiming at target spot coordinates by an MR-guided charged particle beam radiotherapy device, including the following steps.

Construction of a Cost Function

A phase space of a particle beam corresponding to EM steering parameters is simulated on the basis of a Monte Carlo particle transport algorithm. Specifically, a phase space plane in which particle information is recorded is preferably a treatment isocenter plane (at a rotational isocenter of FIG. 2 of the specification), and the number of particles is preferably greater than 300. A cost function $\mathcal{L}_{tot}$, including a position cost function $\mathcal{L}_{pos}$ and a direction cost function $\mathcal{L}_{dir}$, is constructed by means of a difference between a phase space of an ideal particle beam bombarding a target spot and the phase space of the simulated particle beam based on EM steering parameters of a current iteration. These functions are calculated as Formulas (1)-(3):

$$\mathcal{L}_{tot} = \mathcal{L}_{pos} + \lambda \cdot \mathcal{L}_{dir} \tag{1}$$

$$\mathcal{L}_{pos} = |x_0 - \overline{x}| + |y_0 - \overline{y}| \tag{2}$$

$$\mathcal{L}_{dir} = 1 - \cos\overline{\gamma} \tag{3}$$

where $\lambda$ is a weight coefficient of the direction cost function $\mathcal{L}_{dir}$, $x_0$ and $y_0$ are transverse coordinate (a transverse direction referring to a plane perpendicular to an incidence direction of a beam, such as an XY plane in FIG. 2 of the specification, and a longitudinal direction referring to an incidence direction of the beam, such as a negative direction of a Z-axis in FIG. 2 of the specification) positions of a target spot, $\overline{x}$ and $\overline{y}$ are average transverse coordinates of all particles of a particle beam simulated on the basis of EM steering parameters of a current iteration, and $\overline{\gamma}$ is a mean value of angles between incidence directions of all the particles of the particle beam simulated on the basis of the EM steering parameters of the current iteration and the direction of main MR magnetic field, $\overline{x}$, $\overline{y}$ and $\overline{\gamma}$ being all determined by an EM steering parameter set $\mathcal{J}$, and the parameter set $\mathcal{J}$ and the cost function $\mathcal{L}_{tot}$ having a functional relationship of $$\mathcal{L}_{tot}[\mathcal{J}; \lambda] (\mathbb{R}^{2 \times N}_{(-1.0, +1.0)} \to \mathbb{R}).$$

An EM steering parameter commissioning task may be expressed as Formula (4):

$$\underset{\mathcal{J} \in \mathbb{R}^{2 \times N}_{(-1.0, +1.0)}}{\text{minimize}} \mathcal{L}_{tot}[\mathcal{J}; \lambda] \tag{4}$$

where $\mathcal{J}$ is an EM steering parameter set, and N is the number of stages of an EM steering coil set.

Optimization of the EM steering parameters on the basis of an optimization algorithm without gradient information Due to the stochastic nature of a particle transport process, it is difficult to determine an analytical expression of the functional relationship $\mathcal{L}_{tot}[\mathcal{J}; \lambda]$, and it is not possible to obtain gradient information of the cost function $\mathcal{L}_{tot}[\mathcal{J}; \lambda]$ with respect to the input parameter set $\mathcal{J}$. Therefore, $\mathcal{J}$ is randomly corrected according to historical optimization results rather than using gradient information of the cost function $\mathcal{L}_{tot}[\mathcal{J}; \lambda]$ with respect to the EM steering parameter set $\mathcal{J}$ during optimization, a corresponding $\mathcal{L}_{tot}[\mathcal{J}; \lambda]$ is calculated, and an optimization space of $\mathcal{J}$ is searched for or explored.

Determination and output of an optimal steering parameter set

An EM steering parameter set $\mathcal{J}$ with a smallest value of $\mathcal{L}_{tot}[\mathcal{J}; \lambda]$ is taken as an optimal after the preset number of iterations is reached, and an optimal EM steering parameter set of the target spot is outputted.

In the present disclosure, the EM steering parameter set $\mathcal{J}$ includes current directions and current intensities of the multi-stage EM steering coil set; and the EM steering parameter set $\mathcal{J}$ is vectorically encoded, $$\mathcal{J} = \{i_x^1, i_y^1, i_x^2, i_y^2, i_x^3, i_y^3, \ldots\}, \text{ where } i_x^1 \text{ and } i_y^1$$

are normalized currents of the two pairs of orthogonal magnetic field coils in the first-stage EM steering coil set, the normalized currents being obtained using certain preset values, such as corresponding maximum load currents, with values ranging from −1.0 to +1.0, and positive and negative signs indicating current directions, and $$i_x^2 \text{ and } i_y^2, \text{ and } i_x^3 \text{ and } i_y^3$$

represent normalized currents in the second-stage steering coil set and in the third-stage EM steering coil set, respectively.

In the present disclosure, $\lambda$ ranges from 5.0 to 15.0.

In the present disclosure, the optimization algorithm without gradient information is a Bayesian black-box optimization algorithm or a metaheuristic algorithm.

In the present disclosure, the preset number of iterations is 300 or more.

The technical solutions of the present disclosure is stated in detail in combination with a specific example.

Example 1

An MR-guided charged particle beam radiotherapy device as shown in FIGS. 1-2 is adopted. Three energies of 70 MeV, 100 MeV and 150 MeV of high-energy electron beams are used for simulation, and other energies or other types of charged particle beams, such as protons, helium ions or carbon ions, etc., can be used to modify a size of a steering coil set or a current loading on the basis of the example. Combined with an EM steering parameter commissioning method of the present disclosure, a parallel charged particle beam in the same direction as a main magnetic field of MR is generated, realizing precise localization and lateral restraint of the charged particle beam.

The MR-guided parallel charged particle beam radiotherapy device as shown in FIGS. 1-2 includes a vacuum tube 1, a multi-stage EM steering coil set and main magnetic field coils of MR.

The multi-stage EM steering coil set is a triple-stage EM steering coil set, including a first-stage EM steering coil set 2, a second-stage EM steering coil set 3, and a third-stage EM steering coil set 4.

The main magnetic field coil of MR includes an upper group of main magnetic field coils of MR 5 and a lower group of main magnetic field coils of MR 6.

A copper wire used for each of the above coils is 2 mm wide and has a maximum current of 80 A.

A main magnetic field $B_0$ of MR has a magnetic field intensity of about 0.35 T in an imaging and treatment area. A magnetic field intensity in central areas of the first-stage EM steering coil set 2 and the second-stage EM steering coil set 3 is about 0.22 T. A magnetic field intensity in a central area of the third-stage EM steering coil set 4 is about 0.028 T.

Construction of a Cost Function

A cost function is constructed on the basis of the above method, and a particle transport simulation method used for each iteration is preferred to a Monte Carlo simulation particle transport algorithm, which uses a TOPAS library based on an open-source Geant4 code, and uses a C++ code to write linear combination extension packages of multiple magnetic field distributions.

Optimization of EM steering parameters on the basis of an optimization algorithm without gradient information The optimization algorithm for the EM steering parameter commissioning method is a Bayesian black-box optimization with the following steps. (i) Initial setting of $\mathcal{J}_0 = \{0.0, 0.0, 0.0, 0.0, 0.0, 0.0, 0.0\}$ is performed, and a cost function $\mathcal{L}_{tot}[\mathcal{J}_0; \lambda]$ corresponding to $\mathcal{J}_0$ is calculated using Formulas (1)-(3); and according to an initial point ($\mathcal{J}_0, \mathcal{L}_{tot}[\mathcal{J}_0; \lambda]$), a surrogate model is initialized on the basis of a Gaussian process, i.e., the prior distribution of $\mathcal{L}_{tot}[\mathcal{J}; \lambda]$ in a space $$\left(R_{(-1.0,+1.0)}^{2 \times N}\right)$$

of a parameter set $\mathcal{J}$, and an acquisition function is initialized based on the upper confidence bound. (ii) Considering the local exploration and global search comprehensively, a point $\mathcal{J}_i$ is selected from the space of the parameter set $\mathcal{J}$ to maximize the acquisition function for this iteration. (iii) According to $\mathcal{J}_i$, the Monte Carlo particle transport simulation is performed, a phase space file of a particle beam corresponding to $\mathcal{J}_i$ is obtained, and a cost function $\mathcal{L}_{tot}[\mathcal{J}_i; \lambda]$ corresponding to $\mathcal{J}_i$ is calculated using Formulas (1)-(3). (iv) The surrogate model and the acquisition function are updated according to a new data point ($\mathcal{J}_i, \mathcal{L}_{tot}[\mathcal{J}_i; \lambda]$). (v) Steps (ii) to (iv) are repeated until the number of iterations is maximum.

Determination and Output of an Optimal Steering Parameter Set

An EM steering parameter set with a smallest value of $\mathcal{L}_{tot}[\mathcal{J}; \lambda]$ is outputted as an final optimization result after the preset number of iterations is reached. The number of iterations in this example is set to 500.

In this example, 25 target spots are preset in an isocenter plane for all three energies of high-energy electron beams, with coordinates of (0.5,0.5), (0.5,1.5), (0.5,2.5), (0.5,3.5), (0.5,4.5), (1.5,0.5), (1.5,1.5), (1.5,2.5), (1.5,3.5), (1.5,4.5), (2.5,0.5), (2.5,1.5), (2.5,2.5), (2.5,3.5), (2.5,4.5), (3.5,0.5), (3.5,1.5), (3.5,2.5), (3.5,3.5), (3.5,4.5), (4.5,0.5), (4.5,1.5), (4.5,2.5), (4.5,3.5), and (4.5,4.5). All components in the device provided by the present disclosure have a symmetrical structure on the central axis, and the target spots selected in this example are all located in the first quadrant, and the results from the rest of the quadrants can be obtained by symmetrical operation.

Figure 3A:
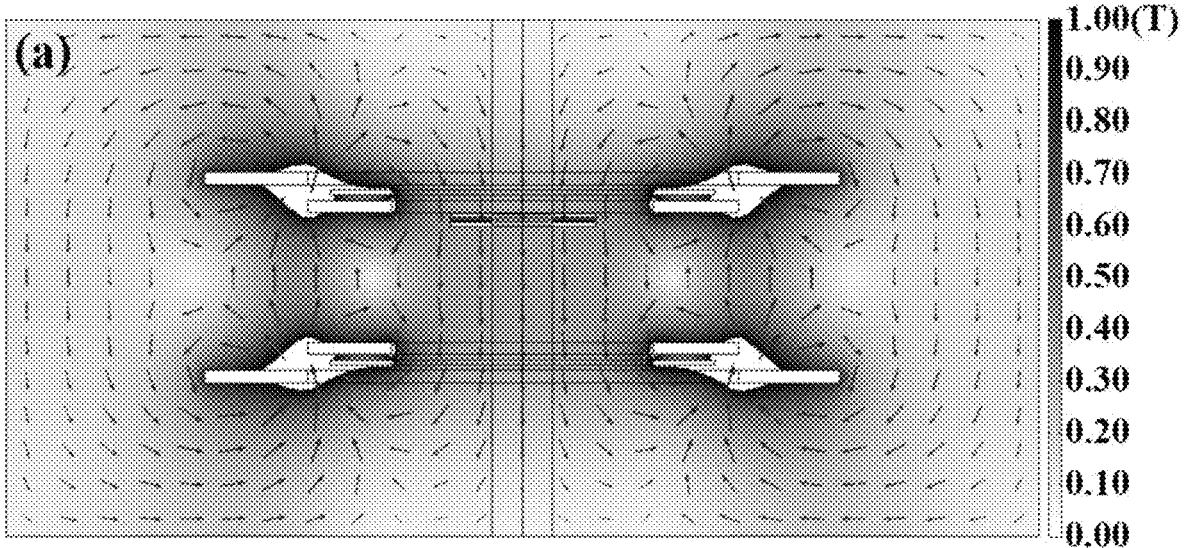
FIG. 3(*a*) shows a two-dimensional magnetic field distribution of an XZ section in an imaging and treatment area (a YZ section is the same as that)
Figure 3B:
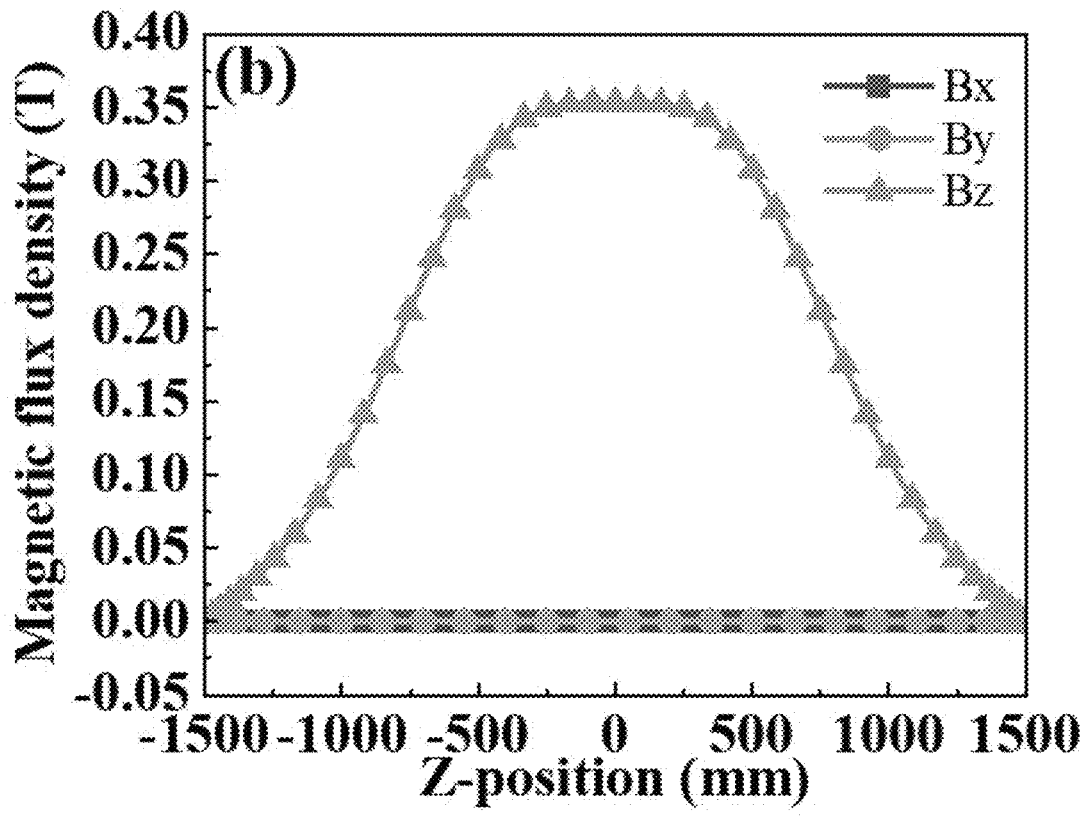
Figure 3C:
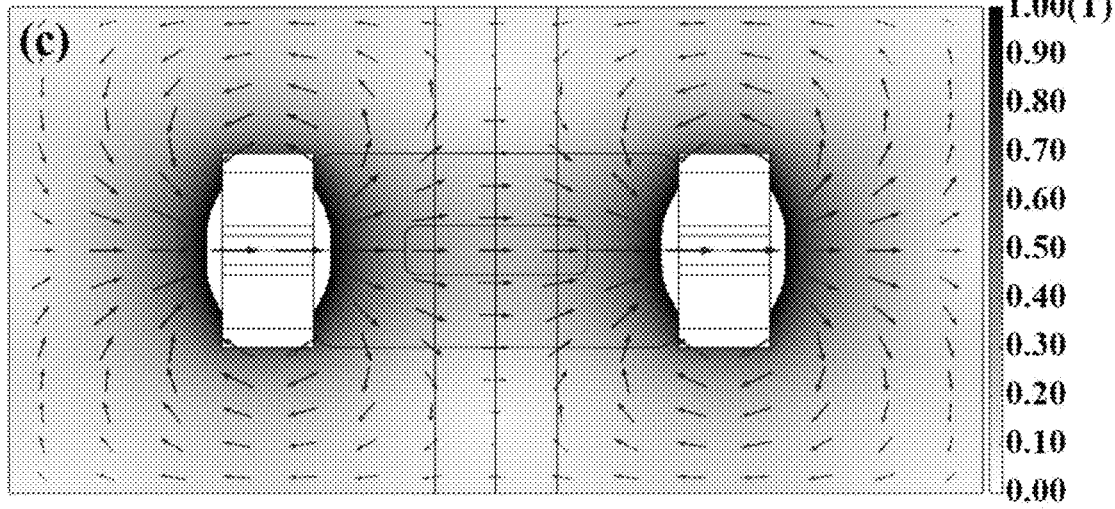
Figure 3D:
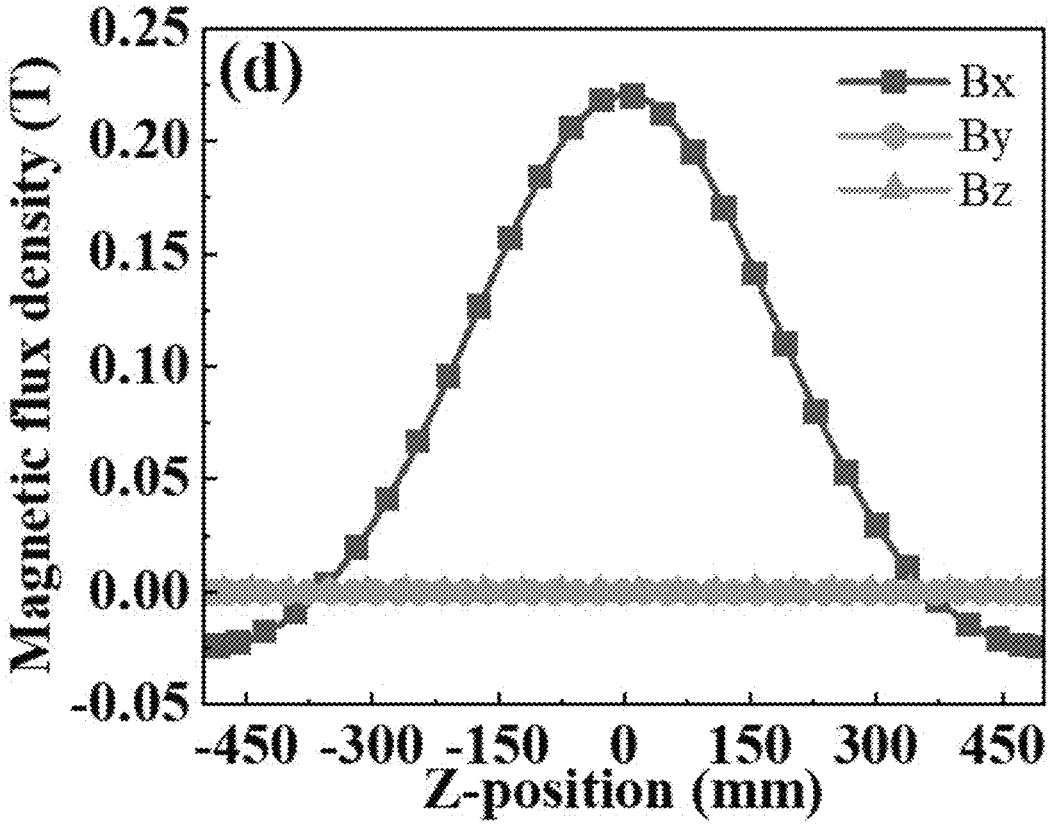
Figure 3E:
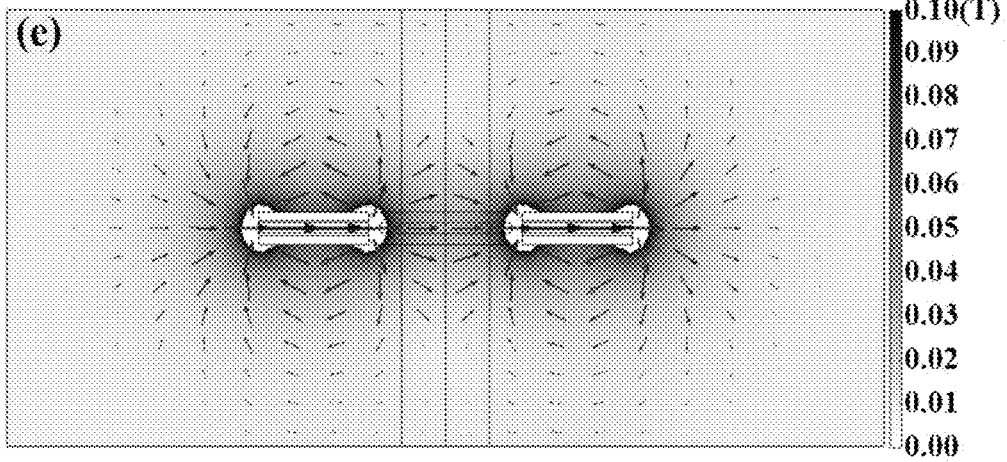
Figure 3F:
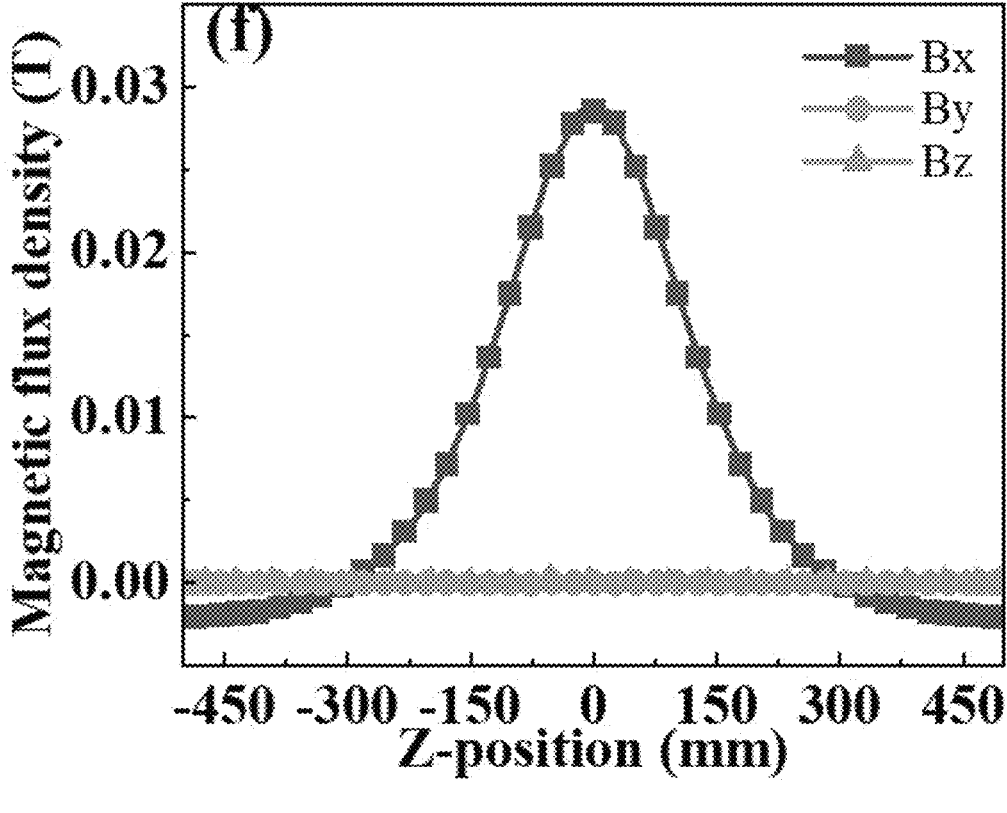

FIGS. 3(a)-3(f) show magnetic field distributions calculated using finite element simulation. FIG. 3(a) and FIG. 3(b) are a two-dimensional magnetic field distribution of an XZ section and a one-dimensional magnetic field distribution of a central axis in an imaging and treatment area (a YZ section is the same as that), respectively. FIG. 3(c) and FIG. 3(d) are a two-dimensional magnetic field distribution of XZ sections and a one-dimensional magnetic field distribution of central axes of the first and second-stage steering coil set, respectively (with only a pair of steering coils in an X-direction energized). FIG. 3(e) and FIG. 3(f) are a two-dimensional magnetic field distribution of an XZ section and a one-dimensional magnetic field distribution of a central axis of the third-stage steering coil set, respectively (with only a pair of steering coils in an X-direction energized).

On the basis of the MR-guided charged particle beam radiotherapy device and the EM steering parameter commissioning method aiming at target spot coordinates provided by the present disclosure, a positional deviation and an angular deviation of a parallel charged particle beam are calculated. A mean value of positional errors of the parallel charged particle beam ranges from 0.2 mm to 0.3 mm, and a mean value of angular errors ranges from 0.4 deg to 0.6 deg. The two kinds of errors are smaller and can meet the clinical requirements, as shown in Table 1. Meanwhile, the lateral confinement effect on the parallel charged particle beams generated based on the present disclosure in Example 1 is verified, as shown in Table 2.

TABLE 1

Positional and angular deviations of parallel charged particle beams generated on the basis of present disclosure in Example 1

| Items | Beam energy (MeV) | | |
| | 70.0 | 100.0 | 150.0 |
|---|---|---|---|
| Positional error (mean value ± standard deviation, mm) | 0.297 ± 0.117 | 0.240 ± 0.139 | 0.266 ± 0.143 |
| Angular error (mean value ± standard deviation, deg) | 0.588 ± 0.358 | 0.446 ± 0.234 | 0.428 ± 0.225 |

TABLE 2

Lateral confinement effect on parallel charged particle beams generated in the present disclosure in Example 1

| Energy (MeV) | Items | Width, mm (percentage of reduction, %) | | | |
| | | Magnetic field free | $1 \times B_0$ | $2 \times B_0$ | $3 \times B_0$ |
|---|---|---|---|---|---|
| 70.0 | Full width at half maximum (FWHM) | 5.496 | 5.036 (8.4) | 3.826 (30.4) | 2.330 (57.6) |
| | Penumbra | 2.723 | 2.484 (8.8) | 1.909 (29.9) | 1.194 (56.2) |
| 100.0 | FWHM | 5.384 | 5.110 (5.1) | 4.486 (16.2) | 3.492 (35.1) |
| | Penumbra | 2.650 | 2.506 (5.4) | 2.202 (16.9) | 1.744 (34.2) |
| 150.0 | FWHM | 5.298 | 5.142 (3.0) | 4.870 (8.1) | 4.372 (17.5) |
| | Penumbra | 2.497 | 2.477 (0.8) | 2.338 (6.4) | 2.083 (16.6) |

Note:
the percentage of reduction = (width in the absence of magnetic field − width in the presence of the corresponding magnetic field)/width in the absence of magnetic field; FWHM: an FWHM of a relative off-axis dose curve; the penumbra: a width between 20% and 80% of the relative off-axis dose curve; and $B_0$ is an intensity of a main magnetic field of MR.

In summary, the present disclosure has provided the MR-guided charged particle beam radiotherapy device and the EM steering parameter commissioning method aiming at target spot coordinates, by coupling the multi-stage EM steering coil set and the main magnetic coils of MR and combined with the EM steering parameter commissioning method aiming at the target spot, the parallel charged particle beams in the same direction as the main magnetic field of MR can be generated, which greatly reduces the effect of the Lorentz force on treatment beams, reducing the difficulty of locating the tumor target spots by the MR-guided charged particle beam and improving the treatment precision; and by means of the main magnetic field of MR, the lateral confinement to the charged particle beams is realized to improve their lateral dose fall-off gradient, better protecting the normal tissues around the tumor and reducing the probability of complications caused by radiotherapy.

The above mentioned is only the better embodiment of the present disclosure, rather than the limitation to the scope of protection of the present disclosure. Within the technical scope disclosed by the present disclosure, any equivalent replacements or variations made by any skilled familiar with the technical field of the present disclosure shall be covered by the scope of protection of the present disclosure.

The invention claimed is:

1. A magnetic resonance (MR)-guided parallel charged particle beam radiotherapy device, capable of generating charged particle beams parallel to a main magnetic field of MR, comprising:

a charged particle beam accelerator, which comprises a linear accelerator, a cyclotron, or a synchrotron, and is configured for generating and accelerating a charged particle beam, allowing energy of the charged particle beam to reach an energy interval required for radiotherapy;

a charged particle beam electromagnetic (EM) steering device, comprising a multi-stage EM steering coil set, the charged particle beam sequentially passing through the multi-stage EM steering coil set to generate a parallel charged particle beam in the same direction as the main magnetic field of MR; and an MR imaging device, comprising:

main magnetic field coils of MR with central axes coinciding with that of the parallel charged particle beams, comprising an upper group of main magnetic field coils of MR and a lower group of main magnetic field coils of MR, an imaging and treatment area being formed therebetween, both the upper group of main magnetic field coils of MR and the lower group of main magnetic field coils of MR comprising imaging coils and shielding coils, the imaging coils being close to the imaging and treatment area, the shielding coils being away from the imaging and treatment area, and the imaging coil having a current opposite to that of the shielding coil in direction;

a gradient magnetic field coil, for generating spatial magnetic field gradient changes to facilitate layer selection and localization of imaging; and a body coil, for generating a radio-frequency field to excite proton resonance in the tissue and receive magnetic resonance relaxation signals to complete a reconstruction.

2. The MR-guided charged particle beam radiotherapy device according to claim 1, wherein the multi-stage EM steering coil set is a triple-stage EM steering coil set arranged sequentially from top to bottom, with each stage containing two pairs of coils that can generate orthogonal steering magnetic fields, a first-stage EM steering coil set deflecting the charged particle beam in a direction of a target spot, a second-stage EM steering coil set having a current opposite to that of the first-stage EM steering coil set to correct a deflection angle of the charged particle beam, and a third-stage EM steering coil set further adjusting an incidence direction of the charged particle beam to compensate for the effect of a fringe magnetic field of MR on the incident charged particle beam, allowing the incidence direction of the charged particle beam to be consistent with the direction of the main magnetic field of the MR imaging and treatment area.

3. The MR-guided charged particle beam radiotherapy device according to claim 2, wherein charged particles in the charged particle beam are electrons, protons, carbon ions or helium ions.

4. An EM steering parameter commissioning method aiming at target spot coordinates by an MR-guided charged particle beam radiotherapy device according to claim 3, comprising the following steps:

(i) construction of a cost function simulating, based on a particle transport algorithm, a phase space of a particle beam corresponding to EM steering parameters, and constructing a cost function $\mathcal{L}_{tot}$ by means of a difference between a phase space of an ideal particle beam bombarding a target spot and a phase space of the simulated particle beam based on EM steering parameters of a current iteration, the cost function comprising a position cost function $\mathcal{J}_{pos}$ and a direction cost function $\mathcal{L}_{dir}$;

$$\mathcal{L}_{tot} = \mathcal{L}_{pos} + \lambda \cdot \mathcal{L}_{dir} \tag{1}$$

$$\mathcal{L}_{pos} = |x_0 - \bar{x}| + |y_0 - \bar{y}| \tag{2}$$

$$\mathcal{L}_{dir} = 1 - \cos \bar{\gamma} \tag{3}$$

where $\lambda$ is a weight coefficient of the direction cost function $\mathcal{L}_{dir}$, $x_0$ and $y_0$ are transverse (a plane perpendicular to an incidence direction of a beam) coordinate positions of a target spot, $\bar{x}$ and $\bar{y}$ are average transverse coordinates of all particles in a particle beam simulated on the basis of EM steering parameters of a current iteration, and $\bar{\gamma}$ is a mean value of angles between incidence directions of all the particles in the particle beam simulated on the basis of the EM steering parameters of the current iteration and the direction of main MR magnetic field, $\bar{x}$, $\bar{y}$ and $\bar{\gamma}$ being all determined by an EM steering parameter set $\mathcal{J}$, the parameter set $\mathcal{J}$ and the cost function $\mathcal{L}_{tot}$ having a functional relationship of $$\mathcal{L}_{tot}[\mathcal{J}; \lambda]\left(R_{(-1.0,+1.0)}^{2 \times N} \to R\right),$$

and an EM steering parameter commissioning task being expressed as Formula (4):

$$\underset{\mathcal{J} \in R_{(-1.0,+1.0)}^{2 \times N}}{\text{minimize}} \mathcal{L}_{tot}[\mathcal{J}; \lambda] \tag{4}$$

where $\mathcal{J}$ is an EM steering parameter set, and N is the number of stages of the EM steering coil set;

(ii) optimization of the EM steering parameters on the basis of an optimization algorithm without gradient information randomly correcting $\mathcal{J}$ according to historical optimization results rather than using gradient information of the cost function $\mathcal{L}_{tot}[\mathcal{J}; \lambda]$ with respect to the EM steering parameter set $\mathcal{J}$ during optimization, calculating a corresponding $\mathcal{L}_{tot}[\mathcal{J}; \lambda]$, and searching for or exploring an optimization space of $\mathcal{J}$; and (iii) determination and output of an optimal steering parameter set taking an EM steering parameter set $\mathcal{J}$ with a smallest value of $\mathcal{L}_{tot}[\mathcal{J}; \lambda]$ as an optimal after the preset number of iterations is reached, and outputting the optimal EM steering parameter set of the target spot.

5. An EM steering parameter commissioning method aiming at target spot coordinates by an MR-guided charged particle beam radiotherapy device according to claim 2, comprising the following steps:

(i) construction of a cost function simulating, based on a particle transport algorithm, a phase space of a particle beam corresponding to EM steering parameters, and constructing a cost function $\mathcal{L}_{tot}$ by means of a difference between a phase space of an ideal particle beam bombarding a target spot and a phase space of the simulated particle beam based on EM steering parameters of a current iteration, the cost function comprising a position cost function $\mathcal{L}_{pos}$ and a direction cost function $\mathcal{L}_{dir}$;

$$\mathcal{L}_{tot} = \mathcal{L}_{pos} + \lambda \cdot \mathcal{L}_{dir} \tag{1}$$

$$\mathcal{L}_{pos} = |x_0 - \bar{x}| + |y_0 - \bar{y}| \tag{2}$$

$$\mathcal{L}_{dir} = 1 - \cos \bar{\gamma} \tag{3}$$

where $\lambda$ is a weight coefficient of the direction cost function $\mathcal{L}_{dir}$, $x_0$ and $y_0$ are transverse (a plane perpendicular to an incidence direction of a beam) coordinate positions of a target spot, $\bar{x}$ and $\bar{y}$ are average transverse coordinates of all particles in a particle beam simulated on the basis of EM steering parameters of a current iteration, and $\bar{\gamma}$ is a mean value of angles between incidence directions of all the particles in the particle beam simulated on the basis of the EM steering parameters of the current iteration and the direction of main MR magnetic field, $\bar{x}$, $\bar{y}$ and $\bar{\gamma}$ being all determined by an EM steering parameter set $\mathcal{J}$, the parameter set $\mathcal{J}$ and the cost function $\mathcal{L}_{tot}$ having a functional relationship of $$\mathcal{L}_{tot}[\mathcal{J}; \lambda]\left(R_{(-1.0,+1.0)}^{2 \times N} \to R\right),$$

and an EM steering parameter commissioning task being expressed as Formula (4):

$$\underset{\mathcal{J} \in R_{(-1.0,+1.0)}^{2 \times N}}{\text{minimize}} \mathcal{L}_{tot}[\mathcal{J}; \lambda] \tag{4}$$

where $\mathcal{J}$ is an EM steering parameter set, and A is the number of stages of the EM steering coil set;

(ii) optimization of the EM steering parameters on the basis of an optimization algorithm without gradient information randomly correcting $\mathcal{J}$ according to historical optimization results rather than using gradient information of the cost function $\mathcal{L}_{tot}[\mathcal{J}; \lambda]$ with respect to the EM steering parameter set $\mathcal{J}$ during optimization, calculating a corresponding $\mathcal{L}_{tot}[\mathcal{J}; \lambda]$, and searching for or exploring an optimization space of $\mathcal{J}$; and (iii) determination and output of an optimal steering parameter set taking an EM steering parameter set $\mathcal{J}$ with a smallest value of $\mathcal{L}_{tot}$ $[\mathcal{J};\lambda]$ as an optimal after the preset number of iterations is reached, and outputting the optimal EM steering parameter set of the target spot.

6. The EM steering parameter commissioning method aiming at target spot coordinates by an MR-guided charged particle beam radiotherapy device according to claim 5, wherein the EM steering parameter set $\mathcal{J}$ comprises current directions and current intensities of the multi-stage EM steering coil set; and the EM steering parameter set is vectorially encoded, $$\mathcal{J} = \{i_x^1, i_y^1, i_x^2, i_y^2, i_x^3, i_y^3, \ldots\}, \text{ where } i_x^1 \text{ and } i_y^1$$

are normalized currents of the two pairs of orthogonal magnetic field coils in the first-stage EM steering coil set, the normalized currents being obtained using certain preset values comprising corresponding maximum load currents, with values ranging from −1.0 to +1.0, and positive and negative signs indicating current directions, and $$i_x^2 \text{ and } i_y^2, \ i_x^3 \text{ and } i_y^3$$

represent normalized currents in the second-stage EM steering coil set and in the third-stage EM steering coil set, respectively.

7. The MR-guided charged particle beam radiotherapy device according to claim 1, wherein an interval between the upper group of main magnetic field coils of MR and the lower group of main magnetic field coils of MR is greater than 60 cm.

8. The MR-guided charged particle beam radiotherapy device according to claim 7, wherein charged particles in the charged particle beam are electrons, protons, carbon ions or helium ions.

9. An EM steering parameter commissioning method aiming at target spot coordinates by an MR-guided charged particle beam radiotherapy device according to claim 8, comprising the following steps:

(i) construction of a cost function simulating, based on a particle transport algorithm, a phase space of a particle beam corresponding to EM steering parameters, and constructing a cost function $\mathcal{L}_{tot}$ by means of a difference between a phase space of an ideal particle beam bombarding a target spot and a phase space of the simulated particle beam based on EM steering parameters of a current iteration, the cost function comprising a position cost function $\mathcal{L}_{pos}$ and a direction cost function $\mathcal{L}_{dir}$;

$$\mathcal{L}_{tot} = \mathcal{L}_{pos} + \lambda \cdot \mathcal{L}_{dir} \tag{1}$$

$$\mathcal{L}_{pos} = |x_0 - \bar{x}| + |y_0 - \bar{y}| \tag{2}$$

$$\mathcal{L}_{dir} = 1 - \cos \bar{\gamma} \tag{3}$$

where $\lambda$ is a weight coefficient of the direction cost function $\mathcal{L}_{dir}$, $x_0$ and $y_0$ are transverse (a plane perpendicular to an incidence direction of a beam) coordinate positions of a target spot, $\bar{x}$ and $\bar{y}$ are average transverse coordinates of all particles in a particle beam simulated on the basis of EM steering parameters of a current iteration, and $\bar{\gamma}$ is a mean value of angles between incidence directions of all the particles in the particle beam simulated on the basis of the EM steering parameters of the current iteration and the direction of main MR magnetic field, $\bar{x}$, $\bar{y}$ and $\bar{\gamma}$ being all determined by an EM steering parameter set $\mathcal{J}$, the parameter set $\mathcal{J}$ and the cost function $\mathcal{L}_{tot}$ having a functional relationship of $$\mathcal{L}_{tot}[\mathcal{J};\lambda]\big(\mathbb{R}_{(-1.0,+1.0)}^{2\times N} \to \mathbb{R}\big)$$

and an EM steering parameter commissioning task being expressed as Formula (4):

$$\underset{\mathcal{J}\in\mathbb{R}_{(-1.0,+1.0)}^{2\times N}}{\text{minimize}} \ \mathcal{L}_{tot}[\mathcal{J};\lambda] \tag{4}$$

where $\mathcal{J}$ is an EM steering parameter set, and W is the number of stages of the EM steering coil set;

(ii) optimization of the EM steering parameters on the basis of an optimization algorithm without gradient information randomly correcting $\mathcal{J}$ according to historical optimization results rather than using gradient information of the cost function $\mathcal{L}_{tot}$ $[\mathcal{J};\lambda]$ with respect to the EM steering parameter set $\mathcal{J}$ during optimization, calculating a corresponding $\mathcal{L}_{tot}$ $[\mathcal{J};\lambda]$, and searching for or exploring an optimization space of $\mathcal{J}$; and (iii) determination and output of an optimal steering parameter set taking an EM steering parameter set $\mathcal{J}$ with a smallest value of $\mathcal{L}_{tot}$ $[\mathcal{J};\lambda]$ as an optimal after the preset number of iterations is reached, and outputting the optimal EM steering parameter set of the target spot.

10. An EM steering parameter commissioning method aiming at target spot coordinates by an MR-guided charged particle beam radiotherapy device according to claim 7, comprising the following steps:

(i) construction of a cost function simulating, based on a particle transport algorithm, a phase space of a particle beam corresponding to EM steering parameters, and constructing a cost function $\mathcal{L}_{tot}$ by means of a difference between a phase space of an ideal particle beam bombarding a target spot and a phase space of the simulated particle beam based on EM steering parameters of a current iteration, the cost function comprising a position cost function $\mathcal{L}_{pos}$ and a direction cost function $\mathcal{L}_{dir}$:

$$\mathcal{L}_{tot} = \mathcal{L}_{pos} + \lambda \cdot \mathcal{L}_{dir} \tag{1}$$

$$\mathcal{L}_{pos} = |x_0 - \bar{x}| + |y_0 - \bar{y}| \tag{2}$$

$$\mathcal{L}_{dir} = 1 - \cos \bar{\gamma} \tag{3}$$

where $\lambda$ is a weight coefficient of the direction cost function $\mathcal{L}_{dir}$, $x_0$ and $y_0$ are transverse (a plane perpendicular to an incidence direction of a beam) coordinate positions of a target spot, $\bar{x}$ and $\bar{y}$ are average transverse coordinates of all particles in a particle beam simulated on the basis of EM steering parameters of a current iteration, and $\bar{\gamma}$ is a mean value of angles between incidence directions of all the particles in the particle beam simulated on the basis of the EM steering parameters of the current iteration and the direction of main MR magnetic field, $\bar{x}$, $\bar{y}$ and $\bar{\gamma}$ being all determined by an EM steering parameter set $\mathcal{J}$, the parameter set $\mathcal{J}$ and the cost function $\mathcal{L}_{tot}$ having a functional relationship of $$\mathcal{L}_{tot}[\mathcal{J}; \lambda](R_{(-1.0,+1.0)}^{2 \times N} \rightarrow \mathbb{R}),$$ (10)

and an EM steering parameter commissioning task being expressed as Formula (4):

$$\underset{\mathcal{J} \in \mathbb{R}_{(-1.0,+1.0)}^{2 \times N}}{\text{minimize}} \quad \mathcal{L}_{tot}[\mathcal{J}; \lambda]$$ (4)

where $\mathcal{J}$ is an EM steering parameter set, and AV is the number of stages of the EM steering coil set;

(ii) optimization of the EM steering parameters on the basis of an optimization algorithm without gradient information randomly correcting $\mathcal{J}$ according to historical optimization results rather than using gradient information of the cost function $\mathcal{L}_{tot}[\mathcal{J}; \lambda]$ with respect to the EM steering parameter set $\mathcal{J}$ during optimization, calculating a corresponding, and $\mathcal{L}_{tot}[\mathcal{J}; \lambda]$ searching for or exploring an optimization space of $\mathcal{J}$; and (iii) determination and output of an optimal steering parameter set taking an EM steering parameter set $\mathcal{J}$ with a smallest value of $\mathcal{L}_{tot}[\mathcal{J}; \lambda]$ as an optimal after the preset number of iterations is reached, and outputting the optimal EM steering parameter set of the target spot.

11. The MR-guided charged particle beam radiotherapy device according to claim 1, wherein charged particles in the charged particle beam are electrons, protons, carbon ions or helium ions.

12. An EM steering parameter commissioning method aiming at target spot coordinates by an MR-guided charged particle beam radiotherapy device according to claim 11, comprising the following steps:

(i) construction of a cost function simulating, based on a particle transport algorithm, a phase space of a particle beam corresponding to EM steering parameters, and constructing a cost function $\mathcal{L}_{tot}$ by means of a difference between a phase space of an ideal particle beam bombarding a target spot and a phase space of the simulated particle beam based on EM steering parameters of a current iteration, the cost function comprising a position cost function $\mathcal{L}_{pos}$ and a direction cost function $\mathcal{L}_{dir}$;

$$\mathcal{L}_{tot} = \mathcal{L}_{pos} + \lambda \cdot \mathcal{L}_{dir}$$ (1)

$$\mathcal{L}_{pos} = |x_0 - \bar{x}| + |y_0 - \bar{y}|$$ (2)

$$\mathcal{L}_{dir} = 1 - \cos \bar{\gamma}$$ (3)

where $\lambda$ is a weight coefficient of the direction cost function, $\mathcal{L}_{dir}$, $x_0$ and $y_0$ are transverse (a plane perpendicular to an incidence direction of a beam) coordinate positions of a target spot, $\bar{x}$ and $\bar{y}$ are average transverse coordinates of all particles in a particle beam simulated on the basis of EM steering parameters of a current iteration, and $\bar{\gamma}$ is a mean value of angles between incidence directions of all the particles in the particle beam simulated on the basis of the EM steering parameters of the current iteration and the direction of main MR magnetic field, $\bar{x}$, $\bar{y}$ and $\bar{\gamma}$ being all determined by an EM steering parameter set $\mathcal{J}$, the parameter set $\mathcal{J}$ and the cost function $\mathcal{L}_{tot}$ having a functional relationship of $$\mathcal{L}_{tot}[\mathcal{J}; \lambda](R_{(-1.0,+1.0)}^{2 \times N} \rightarrow \mathbb{R}),$$

and an EM steering parameter commissioning task being expressed as Formula (4):

$$\underset{\mathcal{J} \in \mathbb{R}_{(-1.0,+1.0)}^{2 \times N}}{\text{minimize}} \quad \mathcal{L}_{tot}[\mathcal{J}; \lambda]$$ (4)

where $\mathcal{J}$ is an EM steering parameter set, and N is the number of stages of the EM steering coil set;

(ii) optimization of the EM steering parameters on the basis of an optimization algorithm without gradient information randomly correcting $\mathcal{J}$ according to historical optimization results rather than using gradient information of the cost function $\mathcal{L}_{tot}[\mathcal{J}; \lambda]$ with respect to the EM steering parameter set $\mathcal{J}$ during optimization, calculating a corresponding $\mathcal{L}_{tot}[\mathcal{J}; \lambda]$ and searching for or exploring an optimization space of $\mathcal{J}$; and (iii) determination and output of an optimal steering parameter set taking an EM steering parameter set $\mathcal{J}$ with a smallest value of $\mathcal{L}_{tot}[\mathcal{J}; \lambda]$ as an optimal after the preset number of iterations is reached, and outputting the optimal EM steering parameter set of the target spot.

13. The MR-guided charged particle beam radiotherapy device according to claim 1, wherein charged particles in the charged particle beam are electrons, protons, carbon ions or helium ions.

14. An EM steering parameter commissioning method aiming at target spot coordinates by an MR-guided charged particle beam radiotherapy device according to claim 13, comprising the following steps:

(i) construction of a cost function simulating, based on a particle transport algorithm, a phase space of a particle beam corresponding to EM steering parameters, and constructing a cost function $\mathcal{L}_{tot}$ by means of a difference between a phase space of an ideal particle beam bombarding a target spot and a phase space of the simulated particle beam based on EM steering parameters of a current iteration, the cost function comprising a position cost function $\mathcal{L}_{pos}$ and a direction cost function $\mathcal{L}_{dir}$;

$$\mathcal{L}_{tot} = \mathcal{L}_{pos} + \lambda \cdot \mathcal{L}_{dir}$$ (1)

$$\mathcal{L}_{pos} = |x_0 - \bar{x}| + |y_0 - \bar{y}|$$ (2)

$$\mathcal{L}_{dir} = 1 - \cos \bar{\gamma}$$ (3)

19 where $\lambda$ is a weight coefficient of the direction cost function $\mathcal{L}_{dir}$, $x_0$ and $y_0$ are transverse (a plane perpendicular to an incidence direction of a beam) coordinate positions of a target spot, $\bar{x}$ and $\bar{y}$ are average transverse coordinates of all particles in a particle beam simulated on the basis of EM steering parameters of a current iteration, and $\bar{\gamma}$ is a mean value of angles between incidence directions of all the particles in the particle beam simulated on the basis of the EM steering parameters of the current iteration and the direction of main MR magnetic field, $\bar{x}$, $\bar{y}$ and $\bar{\gamma}$ being all determined by an EM steering parameter set $\mathcal{I}$, the parameter set $\mathcal{I}$ and the cost function $\mathcal{L}_{tot}$ having a functional relationship $$\mathcal{L}_{tot}[\mathcal{I};\lambda](\mathbb{R}^{2\times N}_{(-1.0,+1.0)} \to \mathbb{R}),$$

of and an EM steering parameter commissioning task being expressed as Formula (4):

$$\underset{\mathcal{I}\in\mathbb{R}^{2\times N}_{(-1.0,+1.0)}}{\text{minimize}} \quad \mathcal{L}_{tot}[\mathcal{I};\lambda] \qquad (4)$$

where $\mathcal{I}$ is an EM steering parameter set, and N is the number of stages of the EM steering coil set;

(ii) optimization of the EM steering parameters on the basis of an optimization algorithm without gradient information randomly correcting $\mathcal{I}$ according to historical optimization results rather than using gradient information of the cost function $\mathcal{L}_{tot}[\mathcal{I};\lambda]$ with respect to the EM steering parameter set $\mathcal{I}$ during optimization, calculating a corresponding $\mathcal{L}_{tot}[\mathcal{I};\lambda]$, and searching for or exploring an optimization space of z,162 ; and (iii) determination and output of an optimal steering parameter set taking an EM steering parameter set $\mathcal{I}$ with a smallest value of $\mathcal{L}_{tot}[\mathcal{I};\lambda]$ as an optimal after the preset number of iterations is reached, and outputting the optimal EM steering parameter set of the target spot.

15. An EM steering parameter commissioning method aiming at target spot coordinates by an MR-guided charged particle beam radiotherapy device according to claim 1, comprising the following steps:

(i) construction of a cost function simulating, based on a particle transport algorithm, a phase space of a particle beam corresponding to EM steering parameters, and constructing a cost function $\mathcal{L}_{tot}$ by means of a difference between a phase space of an ideal particle beam bombarding a target spot and a phase space of the simulated particle beam based on EM steering parameters of a current iteration, the cost function comprising a position cost function $\mathcal{L}_{pos}$ and a direction cost function $\mathcal{L}_{dir}$;

$$\mathcal{L}_{tot} = \mathcal{L}_{pos} + \lambda \cdot \mathcal{L}_{dir} \qquad (1)$$

$$\mathcal{L}_{pos} = |x_0 - \bar{x}| + |y_0 - \bar{y}| \qquad (2)$$

$$\mathcal{L}_{dir} = 1 - \cos\bar{\gamma} \qquad (3)$$

20 where $\lambda$ is a weight coefficient of the direction cost function $\mathcal{L}_{dir}$, $x_0$ and $y_0$ are transverse (a plane perpendicular to an incidence direction of a beam) coordinate positions of a target spot, $\bar{x}$ and $\bar{y}$ are average transverse coordinates of all particles in a particle beam simulated on the basis of EM steering parameters of a current iteration, and $\bar{\gamma}$ is a mean value of angles between incidence directions of all the particles in the particle beam simulated on the basis of the EM steering parameters of the current iteration and the direction of main MR magnetic field, $\bar{x}$, $\bar{y}$ and $\bar{\gamma}$ being all determined by an EM steering parameter set $\mathcal{I}$, the parameter set $\mathcal{I}$ and the cost function $\mathcal{L}_{tot}$ having a functional relationship of $$\mathcal{L}_{tot}[\mathcal{I};\lambda](\mathbb{R}^{2\times N}_{(-1.0,+1.0)} \to \mathbb{R})$$

and an EM steering parameter commissioning task being expressed as Formula (4):

$$\underset{\mathcal{I}\in\mathbb{R}^{2\times N}_{(-1.0,+1.0)}}{\text{minimize}} \quad \mathcal{L}_{tot}[\mathcal{I};\lambda] \qquad (4)$$

where $\mathcal{I}$ is an EM steering parameter set, and N is the number of stages of the EM steering coil set;

(ii) optimization of the EM steering parameters on the basis of an optimization algorithm without gradient information randomly correcting $\mathcal{I}$ according to historical optimization results rather than using gradient information of the cost function $\mathcal{L}_{tot}[\mathcal{I};\lambda]$ with respect to the EM steering parameter set $\mathcal{I}$ during optimization, calculating a corresponding $\mathcal{L}_{tot}[\mathcal{I};\lambda]$, and searching for or exploring an optimization space of $\mathcal{I}$; and (iii) determination and output of an optimal steering parameter set taking an EM steering parameter set $\mathcal{I}$ with a smallest value of $\mathcal{L}_{tot}[\mathcal{I};\lambda]$ as an optimal after the preset number of iterations is reached, and outputting the optimal EM steering parameter set of the target spot.

16. The EM steering parameter commissioning method aiming at target spot coordinates by an MR-guided charged particle beam radiotherapy device according to claim 15, wherein $\lambda$ ranges from 5.0 to 15.0.

17. The EM steering parameter commissioning method aiming at target spot coordinates by an MR-guided charged particle beam radiotherapy device according to claim 15, wherein the optimization algorithm without gradient information is a Bayesian black-box optimization algorithm or a metaheuristic algorithm.

18. The EM steering parameter commissioning method aiming at target spot coordinates by an MR-guided charged particle beam radiotherapy device according to claim 15, wherein the preset number of iterations is 300 or more.

19. An EM steering parameter commissioning method aiming at target spot coordinates by an MR-guided charged particle beam radiotherapy device according to claim 1, comprising the following steps:

(i) construction of a cost function simulating, based on a particle transport algorithm, a phase space of a particle beam corresponding to EM steering parameters, and constructing a cost function $\mathcal{L}_{tot}$ by means of a difference between a phase space of an ideal particle beam bombarding a target spot and a phase space of the simulated particle beam based on EM steering parameters of a current iteration, the cost function comprising a position cost function $\mathcal{L}_{pos}$ and a direction cost function $\mathcal{L}_{dir}$:

$$\mathcal{L}_{tot} = \mathcal{L}_{pos} + \lambda \cdot \mathcal{L}_{dir} \tag{1}$$

$$\mathcal{L}_{pos} = |x_0 - \bar{x}| + |y_0 - \bar{y}| \tag{2}$$

$$\mathcal{L}_{dir} = 1 - \cos\bar{\gamma} \tag{3}$$

where $\lambda$ is a weight coefficient of the direction cost function $\mathcal{L}_{dir}$, $x_0$ and $y_0$ are transverse (a plane perpendicular to an incidence direction of a beam) coordinate positions of a target spot, $\bar{x}$ and $\bar{y}$ are average transverse coordinates of all particles in a particle beam simulated on the basis of EM steering parameters of a current iteration, and $\bar{\gamma}$ is a mean value of angles between incidence directions of all the particles in the particle beam simulated on the basis of the EM steering parameters of the current iteration and the direction of main MR magnetic field, $\bar{x}$, $\bar{y}$ and $\bar{\gamma}$ being all determined by an EM steering parameter set $\mathcal{J}$, the parameter set $\mathcal{J}$ and the cost function $\mathcal{L}_{tot}$ having a functional relationship of $$\mathcal{L}_{tot}[\mathcal{J}; \lambda]\left(\mathrm{R}^{2\times N}_{(-1.0,+1.0)} \to \mathbb{R}\right),$$

and an EM steering parameter commissioning task being expressed as Formula (4):

$$\underset{\mathcal{J} \in \mathbb{R}^{2\times N}_{(-1.0,+1.0)}}{\text{minimize}} \; \mathcal{L}_{tot}[\mathcal{J}; \lambda] \tag{4}$$

where $\mathcal{J}$ is an EM steering parameter set, and N is the number of stages of the EM steering coil set;

(ii) optimization of the EM steering parameters on the basis of an optimization algorithm without gradient information randomly correcting $\mathcal{J}$ according to historical optimization results rather than using gradient information of the cost function $\mathcal{L}_{tot}[\mathcal{J}; \lambda]$ with respect to the EM steering parameter set $\mathcal{J}$ during optimization, calculating a corresponding $\mathcal{L}_{tot}[\mathcal{J}; \lambda]$, and searching for or exploring an optimization space of $\mathcal{J}$; and (iii) determination and output of an optimal steering parameter set taking an EM steering parameter set $\mathcal{J}$ with a smallest value of $\mathcal{L}_{tot}[\mathcal{J}; \lambda]$ as an optimal after the preset number of iterations is reached, and outputting the optimal EM steering parameter set of the target spot.

* * * * *